United States Patent
Yamane et al.

(10) Patent No.: US 8,797,524 B2
(45) Date of Patent: Aug. 5, 2014

(54) MASK INSPECTION METHOD AND MASK INSPECTION APPARATUS

(75) Inventors: Takeshi Yamane, Tsukuba (JP); Tsuneo Terasawa, Kawasaki (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 143 days.

(21) Appl. No.: 13/403,105

(22) Filed: Feb. 23, 2012

(65) Prior Publication Data
US 2012/0218543 A1 Aug. 30, 2012

(30) Foreign Application Priority Data
Feb. 25, 2011 (JP) ................. 2011-040469

(51) Int. Cl.
 G01N 21/00 (2006.01)
 G01J 3/00 (2006.01)
 G01N 21/956 (2006.01)
(52) U.S. Cl.
 CPC ................... G01N 21/956 (2013.01)
 USPC ........................ 356/237.5; 356/51
(58) Field of Classification Search
 USPC .......................... 356/237.1–237.5
 See application file for complete search history.

(56) References Cited

U.S. PATENT DOCUMENTS

| | | | |
|---|---|---|---|
| 6,954,266 B2 | 10/2005 | Tomie | |
| 7,005,649 B1 * | 2/2006 | Tezuka et al. | 250/372 |
| 7,492,449 B2 * | 2/2009 | Ume et al. | 356/237.1 |
| 2001/0019411 A1 * | 9/2001 | Nara et al. | 356/394 |
| 2011/0181868 A1 * | 7/2011 | Stokowski | 356/51 |

FOREIGN PATENT DOCUMENTS

| | | |
|---|---|---|
| JP | 3728495 | 10/2005 |
| JP | 2006-80437 | 3/2006 |
| JP | 2009-251412 | 10/2009 |
| JP | 2010-14635 | 1/2010 |

OTHER PUBLICATIONS

Takeshi Yamane; Toshihiko Tanaka; Tsuneo Terasawa; Osamu Suga, "Actinic EUVL mask blank inspection capability with time delay integration mode", Proc. SPIE 7488, Photomask Technology 2009, 74881B (Sep. 29, 2009).*

Takeshi Yamane; Teruo Iwasaki; Toshihiko Tanaka; Tsuneo Terasawa; Osamu Suga; Toshihisa Tomie, "Signal analysis for the actinic full-field EUVL mask blank inspection system", Proc. SPIE 7122, Photomask Technology 2008, 71222D (Oct. 17, 2008).*

(Continued)

Primary Examiner — Gregory J Toatley
Assistant Examiner — Willie Merrell, II
(74) Attorney, Agent, or Firm — Finnegan, Henderson, Farabow, Garrett & Dunner, LLP

(57) ABSTRACT

According to one embodiment, a method of detecting a defect of a semiconductor exposure mask includes acquiring a background intensity from a surface height distribution of the mask, acquiring a standard background intensity distribution from the background intensity, making light of an arbitrary wavelength incident on the mask, and acquiring an image at a position of interest of the mask, acquiring background intensity raw data, based on a signal intensity of the acquired image at the position of interest and a mean value of image intensity data in a peripheral area of the position of interest, finding a correction coefficient of the signal intensity, based on a ratio of the background intensity raw data to the standard background intensity distribution, correcting the signal intensity by multiplying the signal intensity.

16 Claims, 6 Drawing Sheets

(56) References Cited

OTHER PUBLICATIONS

Yoshihiro Tezuka; Masaaki Ito; Tsuneo Terasawa; Toshihisa Tomie, "Actinic Detection and Screening of Multilayer Defects on EUV Mask Blanks using Dark-field Imaging", Proc. SPIE 5446, Photomask and Next-Generation Lithography Mask Technology XI, 870 (Aug. 20, 2004).*

Mark Fryling; Christopher Frank; Richard McCreery, "Intensity Calibration and Sensitivity Comparisons for CCD/Raman Spectrometers", Applied Spectroscopy, vol. 47, Issue 12, pp. 1965-1974 (1993).*

* cited by examiner

Mask defect inspection system

Personal computer 109

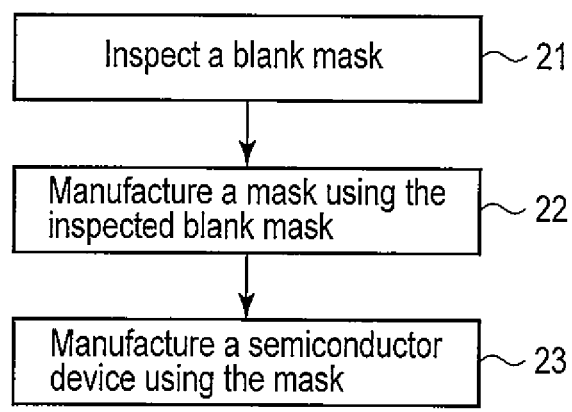
F I G. 10

US 8,797,524 B2

MASK INSPECTION METHOD AND MASK INSPECTION APPARATUS

CROSS-REFERENCE TO RELATED APPLICATIONS

This application is based upon and claims the benefit of priority from prior Japanese Patent Application No. 2011-040469, filed Feb. 25, 2011, the entire contents of which are incorporated herein by reference.

FIELD

Embodiments described herein relate generally to a mask inspection method and a mask inspection apparatus.

BACKGROUND

Patent document 1 (U.S. Pat. No. 3,728,495) discloses "Multilayer film mask defect inspection method and apparatus" as an example of a technique for detecting the position of a defect existing on a semiconductor exposure mask by scattered light.

Patent document 2 (Jpn. Pat. Appln. KOKAI Publication No. 2006-80437) discloses "Mask blanks inspection method and mask blanks inspection tool" as an example of a technique for normalization with use of an intensity in a peripheral region at a time of inspecting a defect existing on a semiconductor exposure mask.

BRIEF DESCRIPTION OF THE DRAWINGS

FIG. 10 is a flow chart illustrating a method for manufacturing a mask for lithography and a method for manufacturing a semiconductor device.

DETAILED DESCRIPTION

Figure 1:
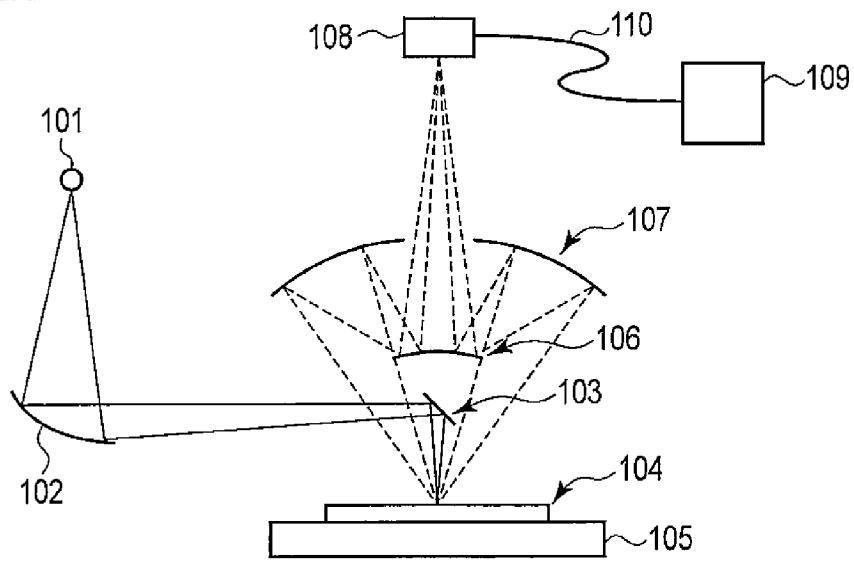
FIG. 1 shows a mask inspection system according to a first embodiment.

In general, according to one embodiment, a method of detecting a defect of a semiconductor exposure mask includes acquiring a background intensity from a surface height distribution of the mask; acquiring a standard background intensity distribution from the background intensity; making light of an arbitrary wavelength incident on the mask, and acquiring an image at a position of interest of the mask; acquiring background intensity raw data, based on a signal intensity of the acquired image at the position of interest and a mean value of image intensity data in a peripheral area of the position of interest; finding a correction coefficient of the signal intensity, based on a ratio of the background intensity raw data to the standard background intensity distribution; correcting the signal intensity by multiplying the signal intensity at the position of interest by the correction coefficient; and determining whether the corrected signal intensity is a predetermined threshold or more.

In the above proposal, in usual cases, a semiconductor exposure mask is fabricated as follows. A opaque film, or a reflective film and an absorption film, are formed by evaporation on a quartz substrate, and a photoresist is coated on the resultant structure. After a desired pattern is drawn on the photoresist, the pattern is developed and etched. Thereby, the opaque film or absorption film is processed to have a desired pattern shape. Thus, the semiconductor exposure mask is obtained. If a particle or the like is present on the quartz substrate, on the opaque film, reflective film or absorption film, or in such films, the opaque capability of the opaque film or the reflecting capability of the reflective multilayer film is degraded, and subsequent development or etching is hindered. As a result, there is concern that the mask pattern has an abnormal shape and the capability of the mask deteriorates.

For example, an exposure mask of extreme-ultraviolet light is a reflective mask. As a reflective film, use is made of a so-called multilayer film in which two kinds of layers with different refractive indexes are alternately stacked. Phases of reflective lights from the respective layers are uniformized, thereby increasing the reflectance.

Thus, when a particle or a pit is present on the quartz substrate, a multilayer film, which is formed thereon, is locally raised or recessed, and there occurs a region where the phases of reflective lights become non-uniform ("phase defect"). There is a tendency that at a time of exposure, this region is transferred onto the wafer. It is necessary, therefore, to inspect the presence/absence of a phase defect in the state of a so-called blank mask in which the multilayer film is formed on the quartz substrate.

For example, the technique disclosed in the above-described patent document 1 is one of the most dominant methods of the technique of inspecting a phase defect of the exposure blank mask for extreme-ultraviolet light. Extreme-ultraviolet light is radiated on the blank mask, and a dark-field image of the blank mask is obtained. When no defect exists on the blank mask, only weak scattered light due to minute asperities, which are called blank mask surface roughness, occurs. On the other hand, when a defect exists, strong scattered light occurs from the defective part, and the defect is observed as a luminescent point in a dark-field image.

Meanwhile, the above-described patent document 2 discloses the technique of normalizing a signal intensity at a position of interest by dividing the signal intensity by a mean value of a detected intensity of a peripheral region (hereinafter referred to as "background intensity"), thereby detecting a defect with use of the normalized signal intensity.

Based on the above knowledge, various embodiments will be described hereinafter with reference to the accompanying drawings. In the description below, common parts are denoted by like reference numerals throughout the drawings.

[First Embodiment]

A mask inspection method and a mask inspection apparatus according to a first embodiment are described.

<1. Structure Example>

1-1. Entire Structure Example

To begin with, referring to FIG. 1, a description is given of an entire structure example of the mask inspection apparatus according to the first embodiment.

As shown in FIG. 1, the mask inspection system of the first embodiment includes an optical system and a personal computer 109 which controls the optical system, the optical system including a light source 101, an elliptic mirror 102, a plane mirror 103, a mask 104, a mask stage 105, a shield 106, a concave mirror 107 and a detector 108.

In this example, the light source 101 is a light source which emits extreme-ultraviolet light.

The elliptic mirror 102 converges the light, which is emitted from the light source 101, to the plane mirror 103.

The plane mirror 103 converges the light, which is converged from the elliptic mirror 102, onto the mask 104.

The mask 104 is disposed on the mask stage 105. In this example, the mask 104 is a blank mask for extreme-ultraviolet exposure.

The mask stage 105 is configured to be able to move the mask 104 in an X direction and a Y direction.

The shield (convex mirror) 106 blocks scattered light of less than an arbitrary radiation angle, which is a part of the light scattered by the mask 104.

The concave mirror 107 collects the scattered light, which has passed by the shield 106, onto the shield 106.

The detector 108 detects light which is collected and focused by the shield 106, captures an image of the focused light, and outputs the intensity of the captured image to the personal computer 109 over a line 110.

The personal computer 109 (controller) functions as a controller for executing a mask inspection method for specifying a defect position by using the intensity of the image of light that is input from the detector 108. The details will be described later.

1-2. Structure Example of Personal Computer

Figure 2:
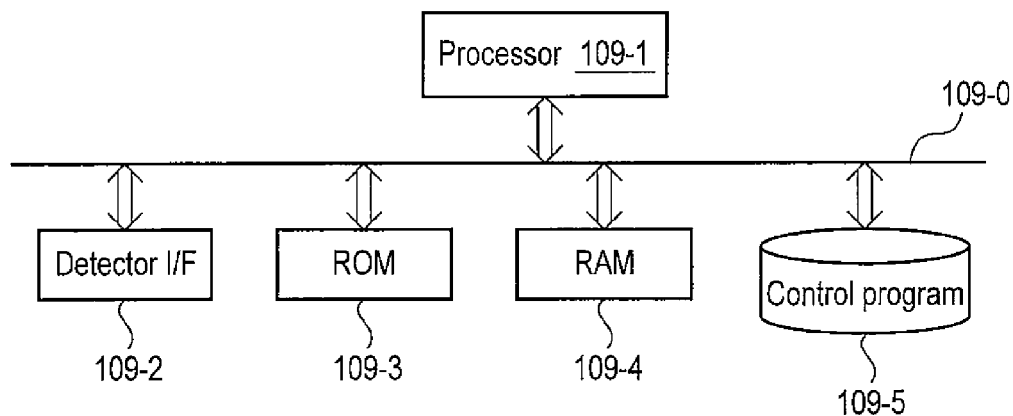
FIG. 2 is a block diagram showing a structure example of a personal computer in FIG. 1.

Next, referring to FIG. 2, a structure example of the personal computer 109 in the first embodiment is described.

As shown in FIG. 2, the personal computer 109 in this embodiment includes a bus 109-0, a processor 109-1, a detector I/F 109-2, a ROM 109-3, a RAM 109-4, and a control program 109-5.

The processor (Processor) 109-1 is electrically connected to the bus 109-0 and controls the entire operation of the personal computer 109.

The detector interface (I/F) 109-2 is electrically connected to the above-described detector 108 via the line 110. The detector I/F 109-2 is electrically connected to the bus 109-0. Thus, an intensity signal, which has been detected by the detector 108, is input to the personal computer 109.

The ROM (Read only memory) 109-3 is electrically connected to the bus 109-0. For example, the control program 109-5 relating to a mask defect inspection method, which will be described later, is nonvolatilely stored in advance in the ROM 109-3.

The RAM (Random access memory) 109-4 is electrically connected to the bus 109-0, and constitutes a work area for storing, e.g. the intensity of the image detected by the detector 108, at the time of executing the mask defect inspection method which will be described later.

The control program 109-5 is a program for executing the respective procedures relating to the mask defect inspection method which will be described later. The control program 109-5 is executed under the control of the processor 109-1.

<2. Mask Defect Inspection Method>

Figure 3:
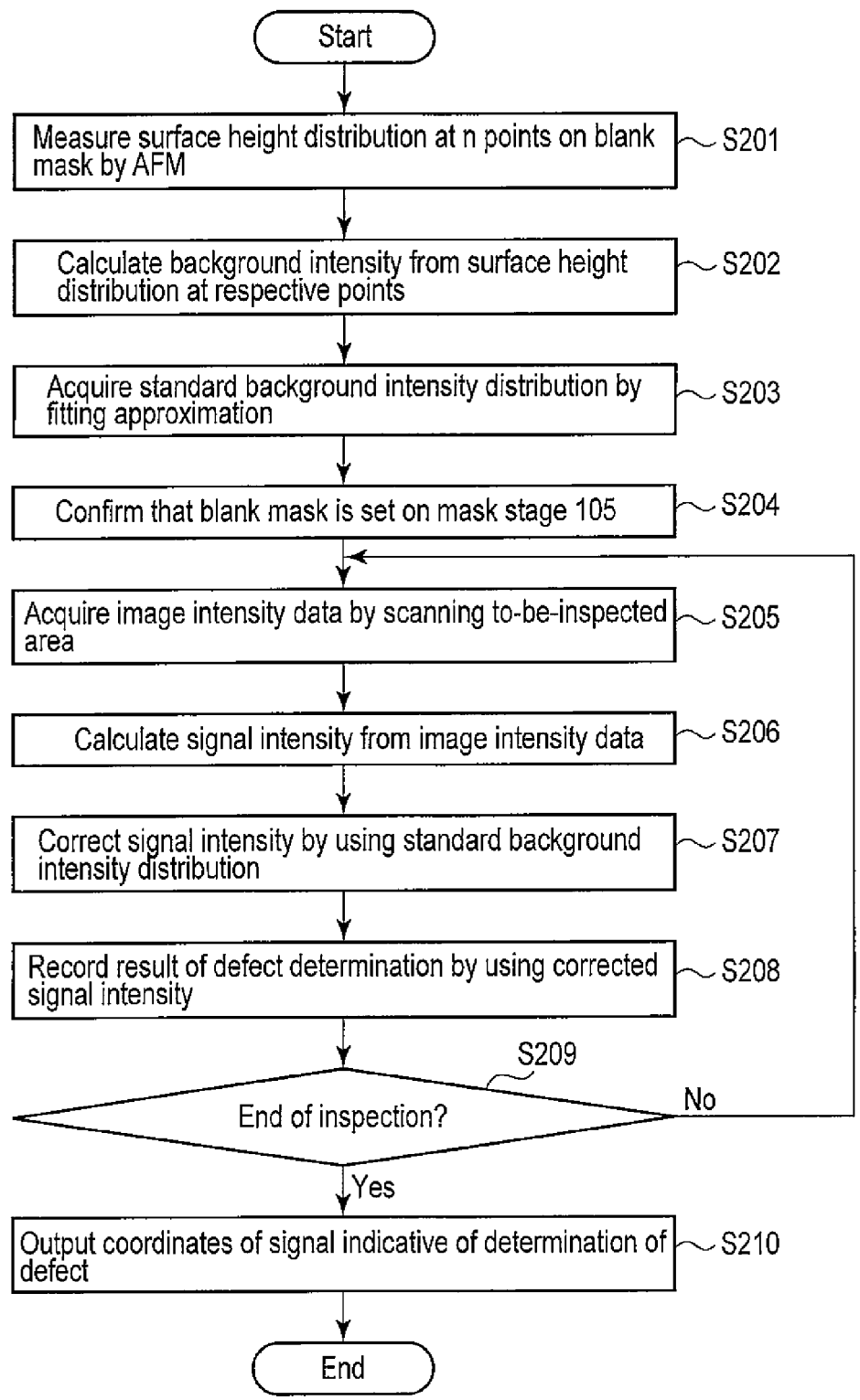
FIG. 3 is a flow chart illustrating a mask inspection method according to the first embodiment.

Next, the mask defect inspection method according to the first embodiment is described. The description will be given with reference to a flow chart of FIG. 3.

(Step S201)

To start with, a surface height distribution is measured by an atomic force microscope (AFM) at n points $(x_1, y_1), (x_2, y_2), \ldots, (x_n, y_n)$ which are substantially uniformly located on the blank mask 104. It should suffice if the number n of measurement points is more than about a number with which a standard background intensity distribution (to be described later) can be obtained with a sufficient precision. The obtained surface height distribution of n points is stored in, for example, the RAM 109-4 in the personal computer 109.

(Step S202)

Then, the obtained surface height distribution is subjected to Fourier transform, and PSD(f) is obtained by the square of an absolute value of the resultant. In this case, f is a spatial frequency, and it is supposed that the PSD has no dependency on an angular direction. A background intensity B at (x, y) can be calculated by the following equation (1). In equation (1), $\lambda$ is wavelength and R is reflectance.

$$B = R\frac{16\pi^2}{\lambda^2}2\pi \int f \times PSD(f)df \qquad \text{Equation (1)}$$

The processor 109-1 of the personal computer 109 calculates equation (1), and finds $B_1, B_2, \ldots, B_n$ at the n points of the surface height distribution stored in the RAM 109-4.

(Step S203)

Figure 4:
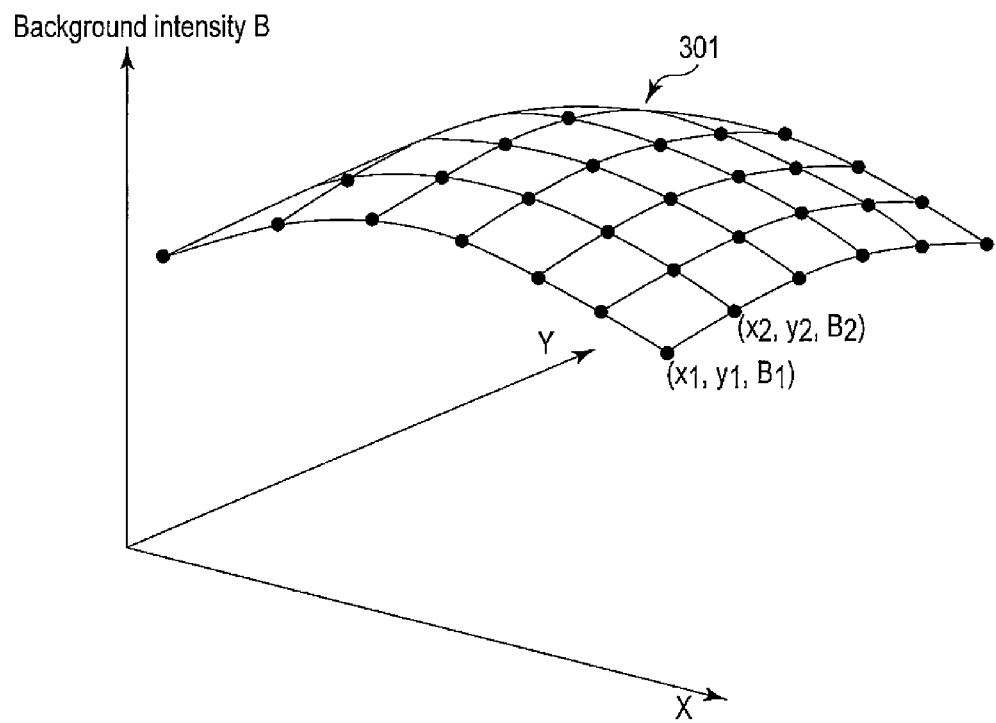
FIG. 4 shows a background intensity distribution according to the first embodiment.

Subsequently, the processor 109-1 executes fitting approximation of the calculated $B_1, B_2, \ldots, B_n$, thereby calculating a standard background intensity distribution $B_{std}(x, y)$ which serves as a standard. For example, the standard background intensity distribution $B_{std}(x, y)$, which is obtained at this time, is as shown in FIG. 4.

The obtained standard background intensity distribution $B_{std}(x, y)$ is stored in, for example, the RAM 109-4 in the personal computer 109.

(Step S204)

Then, the processor 109-1 confirms whether the blank mask 104 that is an inspection target is placed on the mask stage 105.

(Step S205)

Subsequently, the mask stage 105 is moved in a scanning manner, a desired area for inspection, or a to-be-inspected area, is scanned, and image intensity data (I(x, y)) is obtained. The image intensity data (I(x, y)) at a position of interest of the mask, which is obtained in this step in this example, is a dark-field image obtained by the system illustrated in FIG. 1.

To be more specific, in the mask defect inspection system shown in FIG. 1, while the mask stage 105 is being moved in a scanning manner, the detector 108 detects light which is collected and focused by the shield 106 and concave mirror 107, captures an image of the light, and outputs the intensity of the obtained image to the personal computer 109 over the line 110. The obtained data I(x, y) is stored in, for example, the RAM 109-4 in the personal computer 109 via the detector I/F 109-2.

In this embodiment, when this image is obtained, a method called TDI (Time delay integration) is used. The TDI is illustrated, for example, as in FIG. 5.

Figure 5:
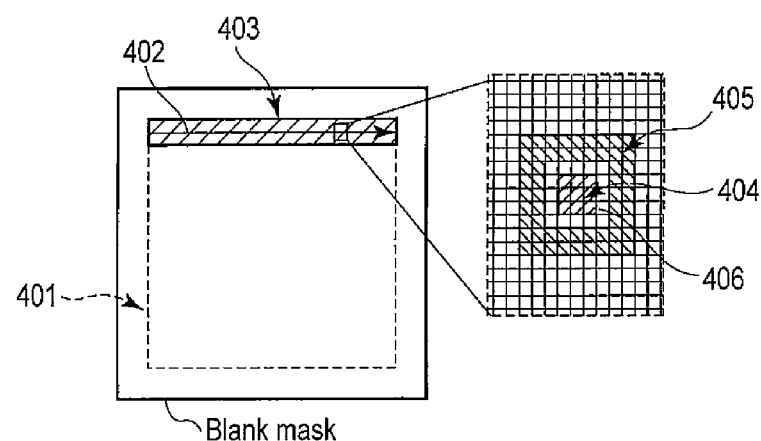
FIG. 5 illustrates one step of the mask inspection method according to the first embodiment.

As shown in FIG. 5, a scanning line 402 included in a desired area 401 for inspection, which is obtained, is scanned, and image intensity data I(x, y) is acquired by the CCD detector 108.

(Step S206)

Subsequently, the processor 109-1 calculates background intensity raw data $(B_{raw}(x, y))$ from the image intensity data I(x, y) obtained in step S205.

To be more specific, an area 403 of the image obtained by scanning one scanning line in FIG. 5 has a width of an image area of the CCD detector 108, and becomes an area along the scanning line. The background intensity raw data $(B_{raw}(x, y))$ can be obtained by calculating a mean value of image intensity data of a pixel area 405 of 7×7 or more and 9×9 or less, centering on a certain pixel 404 of interest of image intensity data I(x, y).

Thus, the processor 109-1 obtains the background intensity raw data ($B_{raw}$(x, y)) by calculating a mean value of image intensity data of the pixel area 405 of 7×7 or more and 9×9 or less, centering on a certain pixel 404 of interest of image intensity data I(x, y) stored in the RAM. The calculated background intensity raw data ($B_{raw}$(x, y)) is stored in, for example, the RAM 109-4 in the personal computer 109.
(Step S207)

Thereafter, the processor 109-1 corrects the signal intensity $S_{raw}$(x, y) by using the standard background intensity distribution $B_{std}$(x, y) obtained in step S203.

To be more specific, the pixel area of 7×7 or more and 9×9 or less in FIG. 5 is determined to be an area which is sufficiently larger than a resolving power of the focusing optical system or a spread of a defect signal due to electron diffusion of the CCD detector 108. Specifically, the processor 109-1 calculates the signal intensity $S_{raw}$(x, y) by finding a sum of (image intensity data I(x, y)–background intensity raw data ($B_{raw}$(x, y)). The signal intensity $S_{raw}$(x, y) is stored in, for example, the RAM 109-4 in the personal computer 109.

Further, the pixel area of 3×3 is determined to be an area having an approximately equal degree of a resolving power of the focusing optical system or a spread of a defect signal due to electron diffusion of the CCD detector 108. Specifically, the processor 109-1 calculates corrected signal intensity $S_{cal}$(x, y) by correcting the signal intensity $S_{raw}$(x, y) stored in the RAM 109-4, by the following equation (2).

$$S_{cal}(x, y) = S_{raw}(x, y) \times \frac{B_{std}(x, y)}{B_{raw}(x, y)} \quad \text{Equation (2)}$$

The calculated corrected signal intensity $S_{cal}$(x, y) is stored in, for example, the RAM 109-4 in the personal computer 109.
(Step S208)

Subsequently, using the calculated corrected signal intensity $S_{cal}$(x, y), the processor 109-1 records the result of defect determination of the mask 104.

To be more specific, the processor 109-1 determines whether the corrected signal intensity $S_{cal}$(x,y) at certain positional coordinates ($x_d$, $y_d$) is a predetermined detection threshold or more. When the corrected signal intensity $S_{cal}$(x, y) at certain positional coordinates ($x_d$, $y_d$) in step S208 is the detection threshold or more, the processor 109-1 determines that a defect is present at the positional coordinates ($x_d$, $y_d$), and records the positional coordinates ($x_d$, $y_d$) as defect coordinates in, for example, the RAM 109-4.
(Step S209)

Then, the processor 109-1 determines whether the inspection has been completed.

To be more specific, when the processor 109-1 has acquired all defect determination results of image intensity data of the to-be-inspected area (Yes), the process advances to the next step S210. On the other hand, when the processor 109-1 has not acquired all defect determination results of image intensity data of the to-be-inspected area (No), the processor 109-1 repeats similar scanning of steps S205 to S208 until the completion of the inspection.
(Step S210)

Subsequently, when the processor 109-1 has acquired all defect determination results of image intensity data of the to-be-inspected area (Yes), the processor 109-1 outputs to the outside the positional coordinates ($x_d$, $y_d$), . . . , ($x_n$, $y_n$) of signals indicative of defects, which have been obtained in step S208. As a result, for example, the processor 109-1 causes a display module (not shown) to display the positional coordinates ($x_d$, $y_d$), . . . , ($x_n$, $y_n$) of signals indicative of defects.
<3. Advantageous Effects>

According to the mask inspection method and mask inspection apparatus of the present embodiment, at least the following advantageous effect (1) can be obtained.

(1) Even in the region where the surface roughness varies, exact correction relative to a light intensity variation of the light source can be executed, and a defect can stably be detected.

As has been described above, the method of detecting a defect of a semiconductor exposure mask according to the first embodiment includes, at least, a step (S202) of acquiring a background intensity from a surface height distribution of the mask; a step (S203) of acquiring a standard background intensity distribution from the background intensity; a step (S205) of making light of an arbitrary wavelength incident on the mask, and acquiring an image at a position of interest of the mask; a step (S206) of acquiring background intensity raw data, based on a signal intensity of the acquired image at the position of interest and a mean value of image intensity data in a peripheral area of the position of interest; a step (S207) of finding a correction coefficient of the signal intensity, based on a ratio of the background intensity raw data to the standard background intensity distribution; a step (S207) of correcting the signal intensity by multiplying the signal intensity at the position of interest by the correction coefficient; and a step (S208, S209) of determining whether the corrected signal intensity is a predetermined threshold or more.

In other words, in the method of inspecting the presence/absence of a defect existing on a semiconductor exposure blank mask according to the first embodiment, the standard background intensity, which serves as a standard, is found from the surface height distribution in advance (S203), and the signal intensity is corrected by multiplying the signal intensity by the ratio of the standard background intensity to the background intensity that is obtained at the time of executing the inspection (S207). By performing the defect inspection by using the corrected signal intensity, the stable defect detection can be performed.

According to the above, even in the region (e.g. the outer peripheral part of the blank mask) where the roughness of the mask surface is deviated and the background intensity varies, there is a merit that the stability of defect detection can be improved, for example, compared to the method of correcting the signal intensity by normalization by the background intensity.

As described above, there is the advantage that even in the region where the surface roughness varies, the correction relative to the light intensity variation of the light source can exactly be performed and defects can stably be detected.

[Second Embodiment (An Example of Application of Thinning-Out Scanning)]

Figure 6:
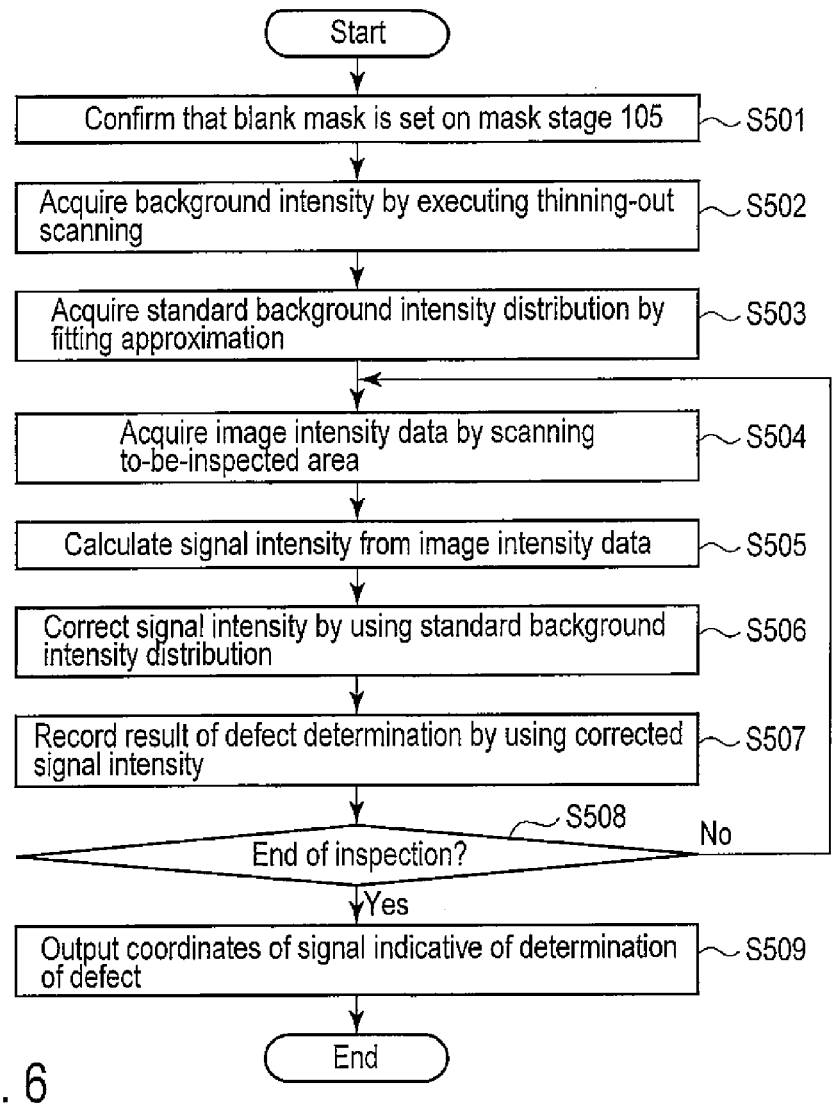
FIG. 6 is a flow chart illustrating a mask inspection method according to a second embodiment.

Next, a mask inspection method and a mask inspection apparatus according to a second embodiment are described with reference to FIG. 6 and FIG. 7. The second embodiment relates to an example in which thinning-out scanning is applied when the background intensity is acquired. A detailed description of parts overlapping those of the first embodiment is omitted.

[Structure Example]

Since the structure example is the same as that of the first embodiment, a detailed description is omitted.

<Inspection Method of Mask Defect>

Next, a mask defect inspection method according to the second embodiment is described. The description is given with reference to a flow chart of FIG. 6.

In the above-described first embodiment, the surface height distribution is acquired by the atomic force microscope (AFM), thereby finding the standard background intensity distribution $B_{std}(x, y)$. The second embodiment differs from the first embodiment in that all scanning lines for acquiring an image of a to-be-inspected area are reduced by thinning-out at substantially equal intervals, and scanning (thinning-out scanning) is executed on the thinned-out scanning lines, thereby acquiring image background intensity data and finding a standard background intensity distribution.

(Step S501)

To start with, the processor 109-1 confirms whether a blank mask that is a target of an inspection is placed on the mask stage 105.

(Step S502)

Then, the processor 109-1 acquires a background intensity by applying the thinning-out scanning.

Figure 7:
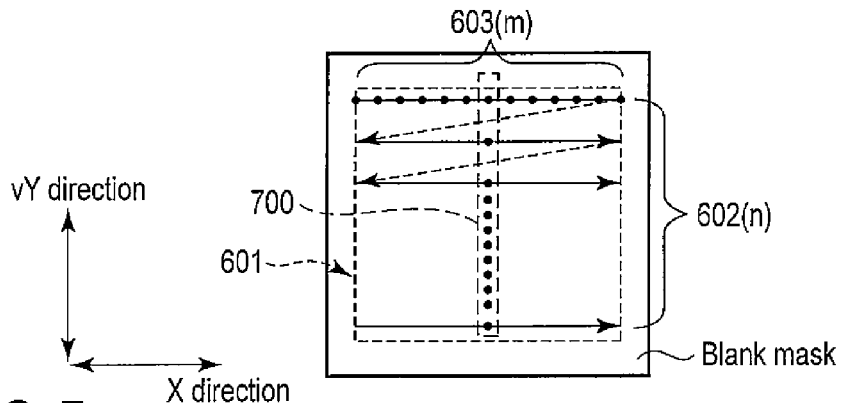
FIG. 7 illustrates one step of the mask inspection method according to the second embodiment.

To be more specific, as shown in FIG. 7, the processor acquires image intensity data by the scanning of an n-number (n: plural) of thinned-out (partly omitted) scanning lines 602, which are obtained by thinning out all scanning lines for acquiring an image of a to-be-inspected area 601 at substantially equal intervals. It is desirable that the number n of thinned-out scanning lines be determined to be such a number that the standard background intensity distribution can be obtained with sufficient precision in a subsequent step S503 and the time that is needed for the scanning becomes sufficiently shorter than a time in which a light intensity variation of a light source occurs.

As regards the obtained image intensity data by the thinning-out scanning, an average intensity in a sufficiently larger area than a defect size at m points (indicated by 603 in FIG. 7) on the respective scanning lines is calculated. As a result, background intensities $B_1, B_2, \ldots, B_{n \times m}(x, y)$ of n×m points in total are found.

The obtained background intensities $B_1, B_2, \ldots, B_{n \times m}(x, y)$ of n×m points in total are stored in, for example, the RAM 109-4 in the personal computer 109.

(Step S503)

Subsequently, the processor 109-1 executes the same fitting approximation, as described above, of the background intensities $B_1, B_2, \ldots, B_{n \times m}(x, y)$, thereby calculating a standard background intensity distribution $B_{std}(x, y)$ which serves as a standard.

The obtained standard background intensity distribution $B_{std}(x, y)$ is similarly stored in, for example, the RAM 109-4 in the personal computer 109.

The subsequent steps S504 to S509 are substantially the same as in the first embodiment, so a detailed description thereof is omitted.

<Advantageous Effects>

As has been described above, according to the mask inspection method and mask inspection apparatus of the second embodiment, at least the same advantageous effect (1) as described above can be obtained.

Furthermore, in the second embodiment, all scanning lines for acquiring an image of a to-be-inspected area are thinned out at substantially equal intervals, and scanning (thinning-out scanning) is executed on the thinned-out scanning lines, thereby acquiring image intensity data (S502) and finding a standard background intensity distribution $B_{std}(x, y)$ (S503).

Therefore, there is no need to acquire the surface height distribution by the atomic force microscope (AFM) as in the first embodiment, and the same advantageous effect can be obtained by a simpler method.

In addition, by executing the thinning-out scanning, the inspection time can be shortened, and a high-speed inspection can advantageously be performed.

Where necessary, this embodiment is applicable.

[Third Embodiment (An Example Relating to Coordinates in Perpendicular Direction to Scanning Direction)]

Next, a mask inspection method and a mask inspection apparatus according to a third embodiment are described. This embodiment relates to an example of acquiring background intensities of coordinates arranged in a perpendicular direction to the scanning direction. A detailed description of parts overlapping those of the first and second embodiments is omitted.

<Structure Example>

Since the structure example is the same as that of the first and second embodiments, a detailed description is omitted.

<Inspection Method of Mask Defect>

Figure 8:
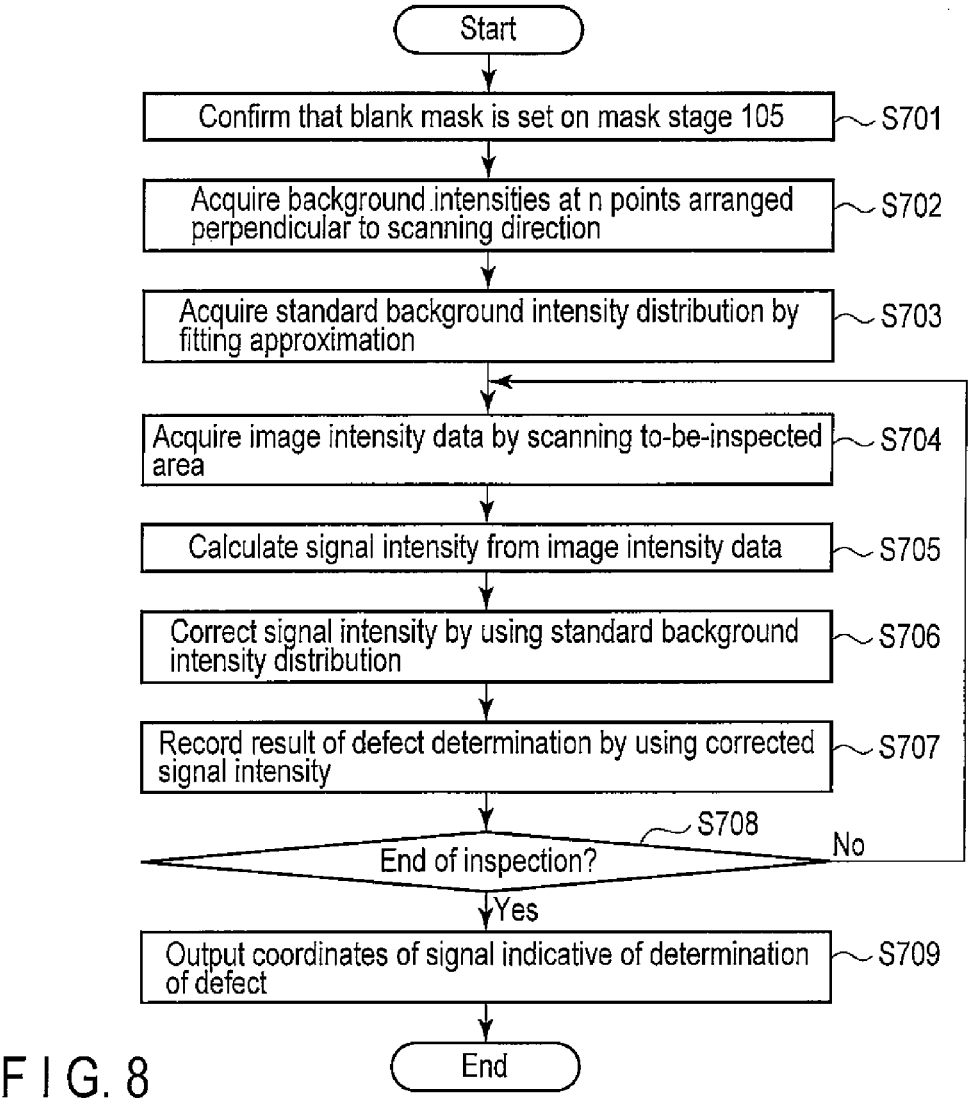
FIG. 8 is a flow chart illustrating a mask inspection method according to a third embodiment.

Next, a mask defect inspection method according to the third embodiment is described. The description is given with reference to a flow chart of FIG. 8.

The third embodiment, as described below, relates to a method of acquiring background intensities of coordinates arranged in a perpendicular direction to the scanning direction, in the case of finding the standard background intensity distribution $B_{std}(x, y)$.

(Step S701)

To start with, the processor 109-1 confirms, in the same manner as described above, whether a blank mask that is a target of an inspection is placed on the mask stage 105.

(Step S702)

Then, the processor 109-1 acquires background intensities at n points which are arranged perpendicular to the scanning direction.

To be more specific, as indicated by a broken line 700 in FIG. 7, when the direction of scanning lines is X, image intensity data of a sufficiently larger area than a defect size is obtained at n points $(x_0, y_1), (x_0, y_2), \ldots, (x_0, y_n)$ in which an X coordinate is $x_0$ and an n-number of Y coordinates are arranged in the Y direction.

Then, by averaging the obtained image intensity data at the n points, background intensities $B_1, B_2, \ldots, B_n(x_0, y)$ at n points are found.

The obtained background intensities $B_1, B_2, \ldots, B_n(y)$ at n points are stored in, for example, the RAM 109-4 in the personal computer, in the same manner as described above.

(Step S703)

Figure 9:
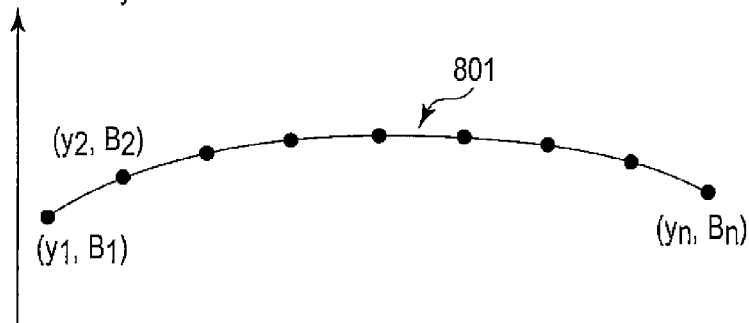
FIG. 9 shows a background intensity distribution according to the third embodiment.

Subsequently, the processor 109-1 executes the same fitting approximation, as described above, of the background intensities $B_1, B_2, \ldots, B_n(y)$, thereby calculating a standard background intensity distribution $B_{std}(y)$, as illustrated in FIG. 9.

The obtained standard background intensity distribution $B_{std}(y)$ is similarly stored in, for example, the RAM 109-4 in the personal computer 109.

(Step S704)

Then, the processor 109 moves the mask stage 105 to scan the to-be-inspected area, thereby acquiring image intensity data $(I(x, y))$. In this case, $(x, y)$ indicates all points in the to-be-inspected area.

To be more specific, while the mask stage 105 is being moved in a scanning manner, the detector 108 in the mask defect inspection system shown in FIG. 1 detects light which is collected and focused by the shield 106, and captures the image of the light. The detector 108 outputs the intensity of the obtained image to the personal computer 109 via the line 110. The obtained data I(x, y) is stored in, for example, the RAM 109-4 in the personal computer 109 via the detector I/F 109-2.

As shown in FIG. 5, the scanning line 402 included in the to-be-inspected area 401, which is obtained, is scanned, and image intensity data I(x, y) is acquired by the CCD detector 108.
(Step S705)

Subsequently, the processor 109-1 calculates the signal intensity from the image intensity data I(x, y).

To be more specific, the background intensity raw data ($B_{raw}$(x, y)) is found by calculating a mean value of image intensity data of the pixel area 405 of 7×7 or more and 9×9 or less, centering on the certain pixel 404 of interest of image intensity data I(x, y) in FIG. 5.

Further, in a 3×3 pixel area 406 entering at the pixel of interest, the signal intensity $S_{raw}$(x, y) is found by the total of (I(x, y)−$B_{raw}$(x, y)).

The obtained signal intensity $S_{raw}$(x, y) is stored in, for example, the RAM 109-4 in the personal computer 109, in the same manner as described above.
(Step S706)

Then, the processor 109-1 corrects the signal intensity using the standard background distribution $B_{std}$(y). At this time, it is assumed that a variation in illumination intensity, which occurs on one scanning line, is ignorable. If y is the same, the same correction coefficient is used.

Specifically, the corrected signal intensity can be found by equation (3) below. As indicated in equation (3), the corrected signal intensity $S_{cal}$(x, y) is obtained by multiplying, by the signal intensity $S_{raw}$(x, y), the ratio of the background intensity raw data ($B_{raw}$($x_0$, y)) to the standard background intensity $B_{std}$(y) at the coordinates ($x_0$, y).

$$S_{cal}(x, y) = S_{raw}(x, y) \times \frac{B_{std}(y)}{B_{raw}(x_0, y)} \quad \text{Equation (3)}$$

The obtained corrected signal intensity $S_{cal}$(x, y) is stored in, for example, the RAM 109-4 in the personal computer 109, in the same manner as described above.

The subsequent steps S707 to S709 are substantially the same as in the first embodiment, so a detailed description thereof is omitted.
<Advantageous Effects>

As has been described above, according to the mask inspection method and mask inspection apparatus of the third embodiment, at least the same advantageous effect (1) as described above can be obtained.

Furthermore, in the third embodiment, the background intensities are acquired at n points ($x_0$, $y_1$), ($x_0$, $y_2$), . . . , ($x_0$, $y_n$) which are arranged perpendicular to the scanning direction (S702).

Thus, when a variation in illumination intensity within a single-scan time is ignorable, the same advantageous effects as in the first and second embodiments can be obtained and a simpler method can be adopted.

In addition, by executing the above-described scanning, the inspection time can further be shortened, and a high-speed inspection can advantageously be performed.

The methods of the above-mentioned embodiments are applicable to a method for manufacturing a mask for lithography and a method for manufacturing a semiconductor device.

FIG. 10 is a flow chart illustrating a method for manufacturing a mask for lithography and a method for manufacturing a semiconductor device. First, a blank mask for extreme-ultraviolet exposure is inspected in the above-mentioned method (S21). Then, a mask for lithography is manufactured using the inspected blank mask (S22). Further, a semiconductor device is manufactured using the manufactured mask for lithography (S23). More specifically, a mask pattern (a circuit pattern) formed on the mask for lithography is transferred to a mask material (e.g., a resist for extreme-ultraviolet exposure) on a semiconductor substrate. Subsequently, the mask material is subject to an exposure process to obtain a mask material pattern. Thereafter, a conductive film, an insulating film, a semiconductor film or the like is etched using the mask material pattern as a mask.

Where necessary, this embodiment is applicable.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A method of detecting a defect of a semiconductor exposure mask, comprising:
    acquiring background intensities at a plurality of points on the mask from a surface height distribution of the mask;
    acquiring a standard background intensity distribution from the background intensities using a fitting approximation;
    making light of an arbitrary wavelength incident on the mask, and acquiring an image at a position of interest of the mask;
    acquiring background intensity raw data, based on a signal intensity of the acquired image at the position of interest and a mean value of image intensity data in a peripheral area of the position of interest;
    finding a correction coefficient of the signal intensity, based on a ratio of the background intensity raw data to the standard background intensity distribution;
    correcting the signal intensity by multiplying the signal intensity at the position of interest by the correction coefficient; and
    determining whether the corrected signal intensity is a predetermined threshold or more.

2. The method of claim 1, wherein acquiring the background intensities includes scanning a reduced number of scanning lines such that a time that is needed for scanning is shorter than a time in which a light intensity variation of a light source occurs.

3. The method of claim 2, wherein acquiring the background intensities includes acquiring only image intensity data in a direction crossing the scanning lines.

4. The method of claim 1, wherein the semiconductor exposure mask is a blank mask for extreme-ultraviolet exposure.

5. The method of claim 1, wherein the light of the arbitrary wavelength is extreme-ultraviolet light.

6. The method of claim 1, wherein the acquired image at the position of interest of the mask is a dark-field image.

7. An apparatus for detecting a defect of a semiconductor exposure mask, the apparatus comprising:
    an optical system configured to make light of an arbitrary wavelength incident on the mask; and a controller configured to control the optical system, the controller being configured to execute:
acquiring background intensities at a plurality of points on the mask from a surface height distribution of the mask;
acquiring a standard background intensity distribution from the background intensities using a fitting approximation;
making light of an arbitrary wavelength incident on the mask, and acquiring an image at a position of interest of the mask;
acquiring background intensity raw data, based on a signal intensity of the acquired image at the position of interest and a mean value of image intensity data in a peripheral area of the position of interest;
finding a correction coefficient of the signal intensity, based on a ratio of the background intensity raw data to the standard background intensity distribution;
correcting the signal intensity by multiplying the signal intensity at the position of interest by the correction coefficient; and
determining whether the corrected signal intensity is a predetermined threshold or more.

8. The apparatus of claim 7, wherein the controller is configured to cause, at a time of acquiring the background intensities, a reduced number of scanning lines such that a time that is needed for scanning is shorter than a time in which a light intensity variation of a light source occurs.

9. The apparatus of claim 8, wherein the controller is configured to, at the time of acquiring the background intensities, acquire only image intensity data in a direction crossing the scanning lines.

10. The apparatus of claim 7, wherein the semiconductor exposure mask is a blank mask for extreme-ultraviolet exposure.

11. The apparatus of claim 7, wherein the light of the arbitrary wavelength is extreme-ultraviolet light.

12. The apparatus of claim 7, wherein the acquired image at the position of interest of the mask is a dark-field image.

13. The apparatus of claim 7, wherein the controller includes:
a bus; and
a processor which is electrically connected to the bus and configured to control an operation of the controller.

14. The apparatus of claim 13, wherein the controller further includes a detector interface which is electrically connected to the bus and a detector.

15. The apparatus of claim 13, wherein the controller further includes a control program for executing procedures relating to a method of inspecting the defect of the mask, the control program being executed according to control of the processor.

16. The apparatus of claim 15, wherein the controller further includes:
a ROM which is electrically connected to the bus and in which the control program is nonvolatilely stored; and
a RAM which is electrically connected to the bus and in which a work area for storing at least the acquired background intensity is formed.

* * * * *